US009315873B2

(12) United States Patent
Beer et al.

(10) Patent No.: US 9,315,873 B2
(45) Date of Patent: Apr. 19, 2016

(54) MARKER VACCINE FOR CLASSICAL SWINE FEVER

(75) Inventors: Martin Beer, Neuenkirchen (DE); Sandra Blome, Sundhagen (DE); Immanuel Leifer, Gross Kiesow (DE)

(73) Assignee: IDT Biologika GmbH, Dessau-Rosslau (DE)

( * ) Notice: Subject to any disclaimer, the term of this patent is extended or adjusted under 35 U.S.C. 154(b) by 191 days.

(21) Appl. No.: 13/698,580

(22) PCT Filed: May 18, 2011

(86) PCT No.: PCT/EP2011/002624
§ 371 (c)(1),
(2), (4) Date: Feb. 1, 2013

(87) PCT Pub. No.: WO2011/144360
PCT Pub. Date: Nov. 24, 2011

(65) Prior Publication Data
US 2013/0129762 A1 May 23, 2013

(30) Foreign Application Priority Data

| | | |
|---|---|---|
| May 18, 2010 | (DE) | 10 2010 017 006 |
| May 18, 2010 | (EP) | 10075205 |
| May 18, 2010 | (EP) | 10075206 |
| May 18, 2010 | (EP) | 10075207 |
| Dec. 17, 2010 | (EP) | 10075759 |
| Dec. 17, 2010 | (EP) | 10075760 |
| Mar. 22, 2011 | (EP) | 11159207 |

(51) Int. Cl.
*A61K 39/12* (2006.01)
*A61K 39/187* (2006.01)
*C12Q 1/70* (2006.01)
*C12N 7/08* (2006.01)
*C07K 14/005* (2006.01)

(Continued)

(52) U.S. Cl.
CPC . *C12Q 1/70* (2013.01); *A61K 39/12* (2013.01); *C07K 14/005* (2013.01); *G01N 33/56983* (2013.01); *A61K 2039/5254* (2013.01); *A61K 2039/542* (2013.01); *A61K 2039/552* (2013.01); *A61K 2039/6081* (2013.01); *C12N 2770/24322* (2013.01); *C12N 2770/24334* (2013.01)

(58) Field of Classification Search
None
See application file for complete search history.

(56) References Cited

U.S. PATENT DOCUMENTS 6,180,109 B1 * 1/2001 Moormann et al. ....... 424/204.1
2008/0292653 A1 11/2008 Orca et al.

OTHER PUBLICATIONS

Everett et al., "Characterisation of experimental infections of domestic pigs with genotype 2.1 and 3.3 isolates of classical swine fever virus," Vet. Microbiol. 142: pp. 26-33 (2010).*

(Continued)

*Primary Examiner* — Benjamin P Blumel
*Assistant Examiner* — M. Franco Salvoza
(74) *Attorney, Agent, or Firm* — Joyce von Natzmer; Agris & von Natzmer LLP

(57) ABSTRACT

The invention relates to a marker vaccine for prophylactic treatment of classical swine fever comprising modified live attenuated classical swine fever virus. The viral amino acid sequence of the TAV-epitope of the E2 protein comprises a different sequence from that of a wild-type classical swine fever virus. The invention relates to pharmaceutical compositions of the marker vaccine. The invention also relates to a method of manufacturing marker vaccines for prevention of classical swine fever using selective antibody pressure.

14 Claims, 4 Drawing Sheets

A

Figure 2:
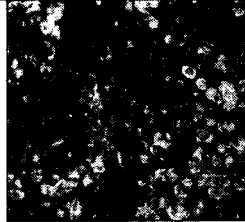
Figure 2:
Figure 2:
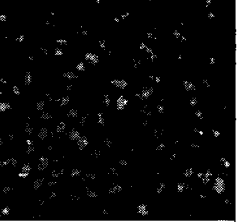
Figure 2:
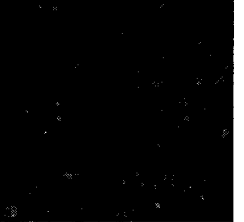
Figure 2:
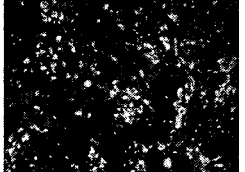
Figure 2:
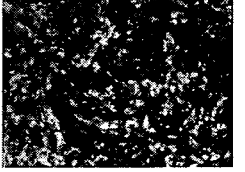
Figure 2:
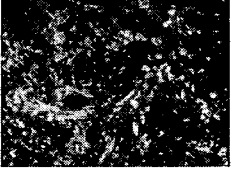
Figure 2:
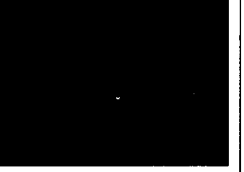

Q7/S10/O11 nucleotide sequence
(SEQ ID NO.1)
CGGGTGTCATAGAGTGCACAGTAGTGAGCTCAACGACTCTGAGAACAGGAGTGGTAAAGA
|||||||||||||||||||| ||||||| |||||||||||||||||| |||||||||||
2841 CGGGTGTCATAGAGTGCACAGCAGTGAGCCCAACGACTCTGAGAACAGAAGTGGTAAAGA 2900
(SEQ ID NO. 2)
C-Strain nucleotide sequence

B

Q7/S10/O11 amino acid sequence
TVVSSTTLRTGVVK (SEQ ID NO. 4)
| || ||||| |||
TAVSPTTLRTEVVK (SEQ ID NO. 5)
C-Strain amino acid sequence

(51) Int. Cl.
*G01N 33/569* (2006.01)
*A61K 39/00* (2006.01)

(56) References Cited

OTHER PUBLICATIONS

Holinka L G et al: "Development of a live attenuated antigenic marker classical swine fever vaccine", in: Virology, Academic Press, Orlando, US, vol. 384, No. 1, Feb. 5, 2009, pp. 106-113.

Reimann I et al: "Characterization of a, new chimeric marker vaccine candidate with a mutated antigenic E2-epitope", IN. Veterinary Microbiology, Elsevier BV, NL, vol. 142, No. 1-2, Apr. 21, 2010, pp. 45-50.

Dong X N et al: "Candidate peptide-vaccines induced immunity against CSFV and identified sequential neutralizing determinants in antigenic domain A of glycoprotein E2", in: Vaccine, Elsevier Ltd, GB, vol. 24, No. 11, Mar. 10, 2006, pp. 1906-1913.

Database UniProt [Online]; May 1, 1991; RecName: Full=Genome polyprotein; Contains: RecName: Full=N-terminal protease; Short=N-pro; EC=3.4.22.-; AltName: Full=Autoprotease p. 20.

Database EMBL [Online], Apr. 28, 2003, "Classical swine fever virus strain Riems, complete genome."

* cited by examiner

Fig. 1

A

Q7/S10/O11 nucleotide sequence
(SEQ ID NO.1)
```
     CGGGTGTCATAGAGTGCACAGTAGTGAGCTCAACGACTCTGAGAACAGGAGTGGTAAAGA
     ||||||||||||||||||||||||| ||||||| |||||||||||||||| |||||||||||
2841 CGGGTGTCATAGAGTGCACAGCAGTGAGCCCAACGACTCTGAGAACAGAAGTGGTAAAGA 2900
```
(SEQ ID NO. 2)
C-Strain nucleotide sequence

B

Q7/S10/O11 amino acid sequence

TVVSSTTLRTGVVK  (SEQ ID NO. 4)
| || |||||| |||
TAVSPTTLRTEVVK  (SEQ ID NO. 5)

C-Strain amino acid sequence

A

| C16 CSF-NS3B & Maus 1:100 Alexa 488 1:1000 | A18Bommeli CSF-E2 & Maus 1:250 Alexa 488 1:1000 | A18Ceditest CSF-E2 & Maus 1:500 Alexa 488 1:1000 | HC34 CSF E2 & Maus 1:80 Alexa 488 1:1000 |
|---|---|---|---|
|  |  |  |  |

B

| C16 CSF-NS3B & Maus 1:100 Alexa 488 1:1000 | A18Bommeli CSF-E2 & Maus 1:250 Alexa 488 1:1000 | A18Ceditest CSF-E2 & Maus 1:500 Alexa 488 1:1000 | Negativ. Kontrolle |
|---|---|---|---|
|  |  |  |  |

Fig. 3

Virus neutralisation test with CSFV strain Rösrath

Q7 — S10 — O11 — C-strain — negative control x-axis: Days of experiment (0dpv, 14dpv, 21dpv, 28dpv, 3dpi, 7dpi)
y-axis: Neutralisation titer (1, 10, 100, 1000)

Fig. 4

Classical swine fever E2 ELISA (Idexx)

SEQUENCE LISTING

<160> NUMBER OF SEQ ID NOS: 5

<210> SEQ ID NO 1
<211> LENGTH: 60
<212> TYPE: DNA
<213> ORGANISM: Flavivirus sp.

<400> SEQUENCE: 1
tctttaccac tcctgttctc agagtcgttg agctcactac tgtgcactct atgacacccg    60

<210> SEQ ID NO 2
<211> LENGTH: 60
<212> TYPE: DNA
<213> ORGANISM: Flavivirus sp.

<400> SEQUENCE: 2
tctttaccac ttctgttctc agagtcgttg ggctcactgc tgtgcactct atgacacccg    60

<210> SEQ ID NO 3
<211> LENGTH: 14
<212> TYPE: PRT
<213> ORGANISM: Flavivirus sp.

<400> SEQUENCE: 3

Thr Ala Val Ser Ser Thr Thr Leu Arg Thr Gly Val Val Lys
1               5                   10

<210> SEQ ID NO 4
<211> LENGTH: 14
<212> TYPE: PRT
<213> ORGANISM: Flavivirus sp.

<400> SEQUENCE: 4

Thr Val Val Ser Ser Thr Thr Leu Arg Thr Gly Val Val Lys
1               5                   10

<210> SEQ ID NO 5
<211> LENGTH: 14
<212> TYPE: PRT

```
<213> ORGANISM: Flavivirus sp.

<400> SEQUENCE: 5

Thr Ala Val Ser Pro Thr Thr Leu Arg Thr Glu Val Val Lys
1               5                   10
```

MARKER VACCINE FOR CLASSICAL SWINE FEVER

This is the U.S. national stage of International application PCT/EP2011/002624, filed May 18, 2011 designating the United States and claiming priority to DE 10 2010 017 006.2, filed May 18, 2010, EP 10075207.0, filed May 18, 2010, EP 10075205.4, filed May 18, 2010, EP 10075206.2, filed May 18, 2010, EP 10075759.0, filed Dec. 17, 2010, EP 10075760.8, filed Dec. 17, 2010, EP 11159207.7, filed Mar. 22, 2011.

The invention relates to a marker vaccine for prophylactic treatment of classical swine fever comprising modified live attenuated classical swine fever virus. In one embodiment of the invention the marker vaccine is characterised in that the viral nucleotide sequence, which encodes the TAV-epitope, and/or the amino acid sequence of the TAV-epitope, comprises a different sequence from that of a disease-associated swine fever virus, so that subjects exhibiting infection with disease-associated swine fever virus can be differentiated from subjects vaccinated with the marker vaccine of the present invention by either serological and/or genomic analytical methods.

BACKGROUND OF THE INVENTION

Classical swine fever (CSF) is an epizootic animal disease that occurs worldwide and has significant political and economic relevance (Vandeputte and Chappuis, 1999). Classical Swine fever, also known as hog cholera or pig plague, is one of the diseases which must be notified Nationally, on the EU-level as well as to the World Organization for Animal Health (OIE) in Paris upon appearance in any member state. Classical swine fever is caused by a small enveloped RNA-virus of the genus *Pestivirus* in the family Flaviviridae. The natural hosts of the swine fever virus are solely domesticated and wild swine species (e.g. European wild boar).

Attempts have been made within the European Union to eradicate CSF through rigorous measures without prophylactic vaccination, which has been forbidden since 1990. Despite the prohibition, vaccination does represent a legally approved option as an emergency vaccination in cases when swine fever appears. In such an event the vaccination should occur via one of the emergency vaccination plans, which have been ratified by the European Union (see Art. 19 of the Counsel Directive 2001/89/EC). Up until now, Romania has been the only country in which an emergency vaccination has been carried out. The reasons for such limited application lie with technical limitations of the marker vaccines available at the present time, such as restrictions in vaccine efficacy, in addition to trade barriers relating to conventionally vaccinated animals (limitation to national marketing). The efficiency of the licensed marker vaccines cannot be compared with modified live vaccines, which exhibit significant advantages, and such inactivated vaccines or subunit vaccines are anyway not suited for emergency vaccination due to later onset of immunity and the need of re-vaccinations.

Considering the expansion of the European Union towards countries in Eastern Europe and ever-increasing globalisation, new strategies have been discussed for potential emergency vaccination, which will play a role in avoiding large scale culling of animals and associated economic losses (Leifer et al., 2009). There is therefore a significant demand for a highly efficient vaccine which allows serological differentiation between vaccinated and non-vaccinated animals and furthermore exhibit all the advantages of traditional modified live vaccines.

Because the first generation of marker vaccines, which were based on the E2 glycoprotein of the CSF virus have only a restricted availability and severe disadvantages like storage conditions, costs, efficacy, there is a large demand for novel marker vaccines. Various candidates for such vaccines have been investigated, such as DNA vaccines, immunogenic peptides, vector vaccines, deletion mutants and chimeric fever viruses (Beer et al., 2007; Dong and Chen, 2007). Most of these marker vaccine candidates exhibit the disadvantage that they are produced via modern methods of genetic modification. Due to the significant consumer fear of genetically modified products, in addition to complicated admission procedures, genetically modified vaccines exhibit significant disadvantages.

Traditional vaccines directed against CSFV do include modified live vaccines. Such vaccines are highly efficient after single application but do not allow the differentiation between vaccinated and infected animals on the basis of a serological profile. Many of these vaccines are based on the classic viral strain "C" or a derivative thereof (so-called "C-strain vaccines"). Additionally, there exist vaccines based on Japanese viral strain "guinea pig exultation-negative (GPE−)", the "Thiverval" strain and the "Mexican PAV" strain, all of which have been used in both regional and international settings (Biome et al, 2006; Greiser-Wilke & Moennig, 2004; van Oirschot, 2003). Extensive data do exist regarding use of the C-strain-based vaccines. It is known that four days after application of the vaccine, a complete protection of the animals against virulent CSFV challenge infection can be demonstrated. Additionally, seven days after vaccination, a complete protection is provided from vertical transmission of challenge virus in carrier animals (de Smit et al., 2001).

The significant disadvantage of the known modified living vaccines is the absolute inability to serologically discriminate between vaccinated and infected animals. In light of this, one task of the present invention is to provide a modified living vaccine which enables discrimination between vaccinated and infected animals.

In the area of marker vaccines, the so called sub-unit vaccines are known in the prior art, which are based upon the recombinant E2 glycoprotein of CSFV. The discrimination test for such vaccines is the enzyme-linked immunosorbent assay (ELISA), in which antibodies directed against the $E^{ms}$ glycoprotein are used to indirectly detect CSF virus infections. At the present time, only one E2-subunit vaccine is available on the market, however, the license was suspended for some months (see EMA report on E2 subunit vaccines).

Regardless of the inability to market such products, such systems exhibit grave biological disadvantages. One such disadvantage is that at least two parenteral immunisations are required before complete protection is conveyed, which renders such vaccines completely incompatible with "bait-vaccinations", where animals are fed in a single dose with vaccine baits. In addition, emergency vaccination campaigns are only reasonable when a protection against wild type CSFV In various experiments using the E2 subunit vaccines, complete protection from vertical transmission was not achieved. A further disadvantage of such systems is that antibodies directed against the glycoprotein $E^{ms}$ are used for serological differentiation and the sensitivity and specificity of such test systems was only ever moderate (Floegel-Niesmann, 2003).

Live attenuated CSF vaccines are known in the art but have until now been hindered by various disadvantages. Most vaccines disclosed in the prior art comprise of foreign DNA and are generated using methods of genetic engineering, otherwise known as recombinant DNA technology, therefore associating serious environmental risk assessment problems with the product. Other CSFV variants are known where amino acids are either substituted or deleted from the wild-type TAV epitope (WO 2010/074575 A2). However, the amino acid residues and/or nucleotides that are modified in the present invention are neither disclosed nor suggested in the prior art.

Multiple passaging has also been used to generate virus variants, which may be used as vaccines, although antibody pressure has not been previously applied. The multiple passaging of virus-infected cultures in order to generate variants as disclosed in the prior art is therefore limited by having to conduct a large number of culture passages and also by a lack of control over which epitope is to be modified (Hulst et al).

Kortekaas et al describe a genetically stable, live attenuated CSF vaccine, which enables the serological differentiation of infected from vaccinated animals. A mutated C-strain was genetically modified using a targeted approach, whereby recombinant DNA technology was used to introduce deletions into the E2 protein of the CSFV. Further mutations were subsequently acquired at various locations within the virus genome via multiple passaging to create strains exhibiting enhanced proliferation. The strains disclosed in Kortekaas et at are genetically engineered viruses, which is a significant disadvantage in light of the complicated admission processes for releasing genetically modified products into the environment.

Holinka et al disclose a double antigenic marker live attenuated CSFV strain "FlagT4vn" which was obtained by combining two genetic determinants of attenuation. FlagT4v harbors a positive antigenic marker, synthetic Flag epitope, introduced via a 19mer insertion in E1 glycoprotein; and a negative marker resulting from mutations of the binding site of monoclonal antibody WH303 (mAbWH303) epitope in the E2 glycoprotein. Intranasal or intramuscular administration of FlagT4v protected swine against virulent CSFV Brescia strain at early (2 or 3 days), and late (28 days) time postinoculation. FlagT4v induced antibody response in pigs reacted strongly against the Flag epitope but failed to inhibit binding of mAbWH303 to a synthetic peptide representing the WH303 epitope. The vaccine disclosed in Holinka relates to a genetically engineered virus that exhibits foreign DNA within its genome (Flag-Tag sequence in addition to associated vector sequence and markers). This represents a significant disadvantage compared to the present invention, which exhibits no foreign or recombinant DNA.

The document WO 2007/143442 A2 describes the effects of mutations within the WH303 epitope of CSFV E2, which change the amino acid sequence of the virulent Brescia CSFV progressively toward the homologous amino acid sequence of BVDV strain NADL. Animals infected with virus mutants were protected when challenged with virulent Brescia virus at 3 and 21 days post vaccination. Modification at this site within the WH303 epitope also allows development of a diagnostic test to differentiate vaccinated from infected animals. Despite these effects, the mutations were introduced using genetic engineering, therefore introducing foreign genetic material into the viral vaccine.

The aforementioned state of the art discloses vaccines that have been engineered via recombinant genetic technology to produce the virus strains. As described above, genetically engineered vaccines are subject to environmental safety concerns and are therefore hindered by complicated admission protocols and fear amongst the general public, therefore providing significant disadvantage to their use.

SUMMARY OF THE INVENTION

In light of the prior art the technical problem underlying the present invention is to provide a marker vaccine for domesticated and wild swine that provides protection against Classical swine fever virus, which enables differentiation between vaccinated and infected animals, produced preferably by conventional technologies. In a preferred embodiment the marker vaccine is not produced via recombinant genetic modification technology.

This problem is solved by the features of the independent claims. Preferred embodiments of the present invention are provided by the dependent claims.

The invention therefore relates to a marker vaccine for prophylactic treatment of classical swine fever comprising modified live attenuated classical swine fever virus.

In a preferred embodiment the invention further relates to a marker vaccine for prophylactic treatment of classical swine fever comprising modified live attenuated classical swine fever virus, characterised in that the viral amino acid sequence of the TAV-epitope of the E2 protein comprises a different sequence from that of a wild-type classical swine fever virus, whereby the viral amino acid sequence exhibits at least one of the following substitutions:
    substitution of amino acid 830; alanine to valine,
    substitution of amino acid 833; proline to serine,
    substitution of amino acid 839; glutamic acid to glycine.

In a preferred embodiment the marker vaccine of the present invention is characterised in that the modified virus is not produced via recombinant DNA methods.

In a preferred embodiment the marker vaccine of the present invention is characterised in that the viral nucleotide sequence exhibits one or more of the following substitutions:
    substitution at nucleotide position 2862; T to C,
    substitution at nucleotide position 2870; G to A,
    substitution at nucleotide position 2889; G to A.

In a preferred embodiment the marker vaccine of the present invention is characterised in that the viral amino acid sequence exhibits one or more of the following substitutions:
    substitution of amino acid 426; in protein $E^{RNS}$; isoleucine to valine,
    substitution of amino acid 576; in protein E1; tyrosine to histidine,
    substitution of amino acid 583; in protein E1; aspartic acid to glutamic acid,
    substitution of amino acid 951: in protein E2; threonine to isoleucine.

In a preferred embodiment the marker vaccine of the present invention is characterised in that the viral nucleotide sequence exhibits one or more of the following substitutions:
    substitution at nucleotide position 1649; A to G,
    substitution at nucleotide position 2099; T to C,
    substitution at nucleotide position 2122; T to G,
    substitution at nucleotide position 3225: C to T.

In a preferred embodiment the marker vaccine of the present invention is characterised in that the viral amino acid sequence of the TAV-epitope comprises the sequence according to SEQ ID NO. 3 or SEQ ID NO. 4.

In a preferred embodiment the marker vaccine of the present invention is characterised in that the viral nucleotide sequence comprises the sequence according to SEQ ID NO. 1.

In another embodiment the marker vaccine of the present invention is characterised in that subjects treated with the vaccine as described herein can be differentiated from subjects infected with disease-associated swine fever virus via analysis of biological samples obtained from said subjects using serological and/or genomic analytical methods.

In another embodiment the marker vaccine of the present invention is characterised in that the genomic analytical method is based upon the polymerase chain reaction (PCR), preferably real-time PCR, whereby primers and/or probes that recognise either the modified and/or disease-associated viral nucleotide sequence are used.

In another embodiment the marker vaccine of the present invention is characterised in that the serological analytical method is based upon an enzyme immunoassay (EIA), preferably an enzyme-linked immunosorbent assay (ELISA), whereby antibodies that bind specifically to either the modified and/or disease-associated TAV-epitope are used.

A further aspect of the invention relates to a marker vaccine, preferably as described herein, obtainable by the generation of viral escape variants of disease-associated or other known swine fever viral strains by application of antibody pressure.

A further aspect of the invention relates to a method of manufacturing a modified live attenuated classical swine fever virus vaccine strain, preferably as described herein, comprising the generation of escape variants of disease-associated or other known swine fever viral strains by application of antibody pressure.

In a preferred embodiment the method of manufacture as described herein is characterised in that the method comprises:
 multiple passaging of cells, preferably embryonal piglet kidney cells, infected with disease-associated swine fever virus in cell culture, and
 simultaneous application of antibodies directed against the TAV-epitope of the E2 protein of disease-associated swine fever virus and/or polyclonal CTAVSPTTL-RTEVVK (SEQ ID NO. 6)-peptide immunised rabbit serum.

The invention further relates to a pharmaceutical composition comprising the marker vaccine as described herein together with a pharmaceutically acceptable carrier.

A further aspect of the invention relates to a marker vaccine as described herein for use as a medicament in the prophylactic treatment (vaccination), preferably via intramuscular injection or oral application, of classical swine fever.

A further aspect of the invention relates to a method for the prophylactic treatment (vaccination) of classical swine fever comprising administration of the marker vaccine as described herein to a subject, preferably a pig, preferably via intramuscular injection or oral application.

Another common situation in which classical swine fever requires vaccination is in response to the detection of field virus infection in pig populations. When infection of pigs occurs, so that the classical swine fever virus is present in either wild or domestic pigs, an emergency vaccination of the surrounding and/or neighbouring pig populations is required. Vaccinations are subsequently carried out for up to 1 to 2 years of all pigs in the surrounding region, whether wild or domesticated, in order to avoid outbreak or large-scale infection of the swine fever virus. The marker vaccine of the present invention is ideally suited for an emergency vaccination in the case of swine fever detection or outbreak. The marker vaccine facilitates fast and effective administration via oral routes, in addition to via injection, and allows discrimination between animals infected with the field virus (fever-associated) and the vaccine.

DETAILED DESCRIPTION OF THE INVENTION

The development of the vaccine according to the present invention is not based on methods of genetic modification but rather the principle that a virus will modify itself in an adaptive manner when placed under selective antibody pressure. The present invention therefore relates to a non-genetically modified live vaccine that provides protection against virulent CSFV, which exhibits all the requirements for a marker vaccine (serologically and genetically distinct). The marker vaccine was engineered by applying selective antibody pressure to different C-strains in cell culture. The generated variants possess preferably three amino acid exchanges in the E2 TAV epitope and two compensatory exchanges in the E1 protein. Stability of these variants was proven by more than ten cell culture passages in roller drums and e.g. intramuscular vaccination of pigs led to complete protection against a highly virulent challenge strain. Furthermore, direct DIVA is enabled by serological and/or genetic techniques, for example by distinct immunofluorescent staining and real-time reverse transcription polymerase chain reaction (rRT-PCR) systems. Also, indirect DIVA might be achievable by optimizing commercial E2-ELISAs (e.g. by changing the cut off values) or developing TAV-specific peptide-ELISA systems. Thus, a non-genetically modified live marker vaccine against CSFV is presented.

Production of the vaccine according to the present invention occurs as follows:

Naturally appearing C-strain "Riems" escape variants are selected in a cell culture system (IFN-embryonal piglet kidney cells) via passaging the C-strain virus during application of E2-TAV specific antibodies and polyclonal CTAVSPTTL-RTEVVK (SEQ ID NO. 6)-peptide immunised rabbit serum.

The applied antibodies, in addition to the antibodies contained in the peptide-treated polyclonal rabbit serum, recognise the TAV-epitope in the E2 protein of the CSF virus specifically, and through binding to this epitope neutralise the CSF (C-strain) virus. The CSFV exhibits a high mutation rate due to their RNA nature. Under the selection pressure of providing neutralising antibodies, viruses, which undergo mutation in the epitope to which the antibodies bind (in this case, the TAV-epitope) are selected, whereby the unchanged wild type viruses are neutralised. Via multiple passaging under various antibody and rabbit serum concentrations and mixtures, various mutated virus isolates can be selected.

Viruses with a substitution in the TAV-epitope were first selected. Through further passaging of these viruses under various kinds of antibody pressure an isolate was selected, which exhibited two substitutions in the TAV-epitope and a single compensatory substitution in the E1 protein (the interaction between E1 and E2 is important for the virus structure). These viruses were put under further antibody pressure, which led to isolation of viruses with three substitutions in the TAV-epitope in addition to two compensatory substitutions in the E1 protein. The resulting viruses (C-strain "Riems" Q7, C-strain "Riems" S10 and C-strain "Riems" O11) exhibited substitutions in the E2 protein at positions 2862, 2870 and 2889, 3225, in addition to changes in the E1 protein at positions 2099 and 2122, in addition to a substitution in the $E^{RNS}$ protein at position 1649.

TABLE 1

Further information to the TAV escape variants

| Genome position | Nucleotide Substitution (C-strain to escape variant) | Amino Acid | Protein | Amino Acid Substitution (resulting amino acid exchange from C-strain to escape variant) |
|---|---|---|---|---|
| 1649 | A to G | 426 | $E^{RNS}$ | Isoleucine to valine |
| 2099 | T to C | 576 | E1 | Tyrosine to histidine |
| 2122 | T to G | 583 | E1 | Aspartic acid to glutamic acid |

TABLE 1-continued

Further information to the TAV escape variants

| Genome position | Nucleotide Substitution (C-strain to escape variant) | Amino Acid | Protein | Amino Acid Substitution (resulting amino acid exchange from C-strain to escape variant) |
|---|---|---|---|---|
| 2862 | T to C | 830 | E2 (TAV epitope) | Alanine to valine |
| 2870 | G to A | 833 | E2 (TAV epitope) | Proline to serine |
| 2889 | G to A | 839 | E2 (TAV epitope) | Glutamic acid to glycine |
| 3225 | C to T | 951 | E2 | Threonine to isoleucine |

The changes in nucleotide sequence enable a real time RT-PCR system, that can differentiate between the variants (Q7, S10, O11) and the field isolates.

The changes in amino acid sequence enable the differentiation between the variants (Q7, S10, O11) and the field isolates on the basis of antibody binding, whereby the antibodies used for the neutralisation (A18 antibodies) no longer bind to the variants but do bind all field isolates due to the highly conserved TAV epitope in CSFV. Antibodies generated against the modified TAV peptide sequence (exhibiting mutations of the present invention) can also be used for differentiation between infectious virus and vaccine, whereby the antibodies directed against the variants will bind the modified virus vaccine of the present invention and provide positive identification of vaccinated animals, but will not bind the field isolates.

TABLE 2

Sequences of the present invention:

| SEQ ID NO | Strain | DNA/protein | Sequence 5'-3' |
|---|---|---|---|
| SEQ ID NO. 1 | Q7/S10/O11 | DNA | TCTTTACCACTCCTGT TCTCAGAGTCGTTGAG CTCACTACTGTGCACT CTATGACACCCG |
| SEQ ID NO. 2 | C-strain | DNA | TCTTTACCACTTCTGT TCTCAGAGTCGTTGGG CTCACTGCTGTGCACT CTATGACACCCG |
| SEQ ID NO. 3 | B5/2 | protein | TAVSSTTLRTGVVK |
| SEQ ID NO. 4 | Q7/S10/O11 | protein | TVVSSTTLRTGVVK |
| SEQ ID NO. 5 | C-strain | protein | TAVSPTTLRTEVVK |

The present invention relates to a modified swine fever virus that may comprise of any or all of the possible combinations of mutations and substitutions disclosed herein. The examples and experimental support provided herein demonstrate that viral strains were generated that exhibit only a sub-set of all the substitutions listed in Table 1. These viral strains exhibit a protective effect in addition to being able to be used as markers, therefore fulfilling the objective of the present invention. The preferred strains of the present invention relate to strains comprising sub-sets of the disclosed substitutions, in addition to those strains that exhibit all of the disclosed substitutions.

It was entirely surprising that the combinations of one or more of the specific genetic modifications (derived via natural processes as a result of antibody pressure) would lead to the beneficial properties of the marker vaccine as described herein. The prior art reveals some similar modifications, but nothing known in the art would suggest that the particular residues modified in the present invention would provide a particularly effective protection from CSFV infection. Their unique combinations lead to the set of properties described that enable the invention to act as a vaccine capable of differentiating between infected and vaccinated animals.

It was unknown that such selective pressure as applied in the present application via antibody treatment would lead to the precise modification described herein. The combinations of genetic modifications as described herein function together, providing the synergetic effect of compensatory mutations that maintain protein structure, whilst allowing the TAV residues to mutate and thus provide the marker characteristics required by the task of the present invention.

The term genetic engineering relates to genetic modification or manipulation of an organism's genome, for example by introducing foreign nucleic acid material, such as DNA or RNA, or synthetic nucleic acid sequences into the host genome. This technology is also known as recombinant DNA technology.

The term attenuated virus refers to virus that has been modified, in any manner of ways, so that the virus is less harmless and/or less virulent in comparison to the wild type (disease-associated) virus. For example fewer disease associated symptoms appear in subjects infected with attenuated virus in comparison to wild type virus.

The term antibody pressure or selective antibody pressure in terms of the present invention relates to the application of antibodies during cell culture, preferably over multiple passages, that are directed to one or more specific epitopes of the virus. Such antibodies can be any kind of antibody known in the art, either mono or polyclonal, or may be contained in serum from animals treated with a peptide of interest, for example the target epitope. Such antibodies are often termed neutralising antibodies. Under the selection pressure of providing neutralising antibodies, viruses, which undergo mutation in the epitope to which the antibodies bind (in this case, the TAV-epitope) are selected due to their growth advantage, as the antibodies no longer bind to said epitope and therefore no longer provide a limiting or neutralising effect, whereby the unchanged wild type viruses are neutralised by the antibodies are subsequently selectively disadvantaged in culture.

Those viruses, which undergo mutation in the epitope to which the antibodies bind (in this case, the TAV-epitope), are commonly referred to as escape variants. These variants are subject matter of the present invention, and are genetically and serologically distinct from wild type virus.

The term multiple passaging refers to the cell culture practice of passaging (also known as subculture or splitting cells) over a number of times, whereby a small number of cells is transferred into a new vessel, preferably with fresh media, or by dilution of cell cultures into new media, over a number of times so that the cell cultures are allowed to continue in growth without the associated effects of high cell density in cultures.

In light of the marker vaccine, the invention may also relate to a unified group of inventions that are combined by a single inventive concept. The marker vaccine, the virus itself and pharmaceutical compositions thereof, their use in treating animals for vaccination and methods for producing the virus all fall under a general inventive concept. The novel and inventive marker vaccine described herein both enables and unifies all the aspects of the present invention, so that the various embodiments described herein fall within a single unifying invention.

Where nucleotide sequences are provided in the present application, the sequence listings are intended to encompass both the corresponding RNA and DNA sequences. Although some nucleotide sequences are provided as DNA sequences, the corresponding RNA sequences (for example where the virus genome exhibits an RNA molecule) are intended to be encompassed in the present invention. The nucleotide sequences of the present invention also encompass the complementary sequences of those listed, for example the complementary sequence that could via Watson-Crick base pairing bind to the listed sequence. Corresponding complementary, RNA and/or DNA sequences require no inventive effort to convert one from the other and are easily within reach of one skilled in the art.

The administration procedure for the viral vaccine of the present invention, compositions of the invention such as pharmaceutical, immunological, antigenic or vaccine compositions or therapeutic compositions, can be administered via parenteral routes, such as intradermal, intramuscular or subcutaneous application methods. Such an administration enables a systemic immune response, or humoral or cell-mediated immune responses. The vaccine according to the present invention can also be administered by oral routes, such as being incorporated in animal feed, enabling simple and effective immunisation of large populations, e.g. European wild boar.

The preferred methods of application relate to either subcutaneous application or intramuscular application, preferably by injection, and oral application.

More generally, the inventive viral vaccine compositions or therapeutic compositions can be prepared in accordance with standard techniques well known to those skilled in the pharmaceutical or veterinary art.

A therapeutically effective amount of such compositions can be administered in dosages and by techniques well known to those skilled in the medical or veterinary arts taking into consideration such factors as the age, sex, weight, species and condition of the particular subject, and the route of administration. The compositions can be administered alone, or can be co-administered or sequentially administered with compositions, e.g., with "other" immunological, antigenic or vaccine or therapeutic compositions thereby providing multivalent or "cocktail" or combination compositions of the invention and methods employing them. Again, the ingredients and manner (sequential or co-administration) of administration, as well as dosages can be determined taking into consideration such factors as the age, sex, weight, species and condition of the particular subject, and, the route of administration.

Examples of compositions of the invention include liquid preparations for orifice, e.g., oral, nasal, anal, vaginal, per-oral, intragastric, etc., administration such as suspensions, syrups or elixirs; and, preparations for parenteral, subcutaneous, intradermal, intramuscular or intravenous administration (e.g., injectable administration) such as sterile suspensions or emulsions.

In such compositions the CSFV variants may be in admixture with a pharmaceutically acceptable carrier, diluent, or excipient such as sterile water, physiological saline, glucose or the like. The compositions can also be lyophilized. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired.

SHORT DESCRIPTION OF THE FIGURES

FIG. 1: Sequence comparisons
FIG. 2: Indirect Immunofluorescence analysis
FIG. 3: VNT with the CSFV strain Rösrath
FIG. 4: Idexx E2-ELISA with pig serum from the 06/10 animal study

DETAILED DESCRIPTION OF THE FIGURES

FIG. 1: Sequence comparisons. A) Nucleotide sequence comparison of the TAV-epitope region between the Q7, S10, O11 variants and the C-strain field isolate. B) Amino acid sequence comparison of the TAV-epitope region between the Q7, S10, O11 variants and the C-strain field isolate.

FIG. 2: Indirect Immunofluorescence analysis. A) Analysis of the E2 escape mutants, B5/2 Passage 2 (precursor virus for Q7, S10 and O11, which exhibits only 2 substitutions in the TAV-epitope). B) Analysis of the C-strain virus.

FIG. 3: Three weeks after immunisation all animals, with the exception of one animal in the S10 group and one animal in the O11 group, showed neutralising antibodies. 7 days after infection the immunised animals demonstrated a VNT titre of 640 or larger. The lowest titre was 320, shown by one animal in the TAV mutant immunised group. The non-immunised control animals exhibited no titre in the VNT against Rösrath.

Figure 4:
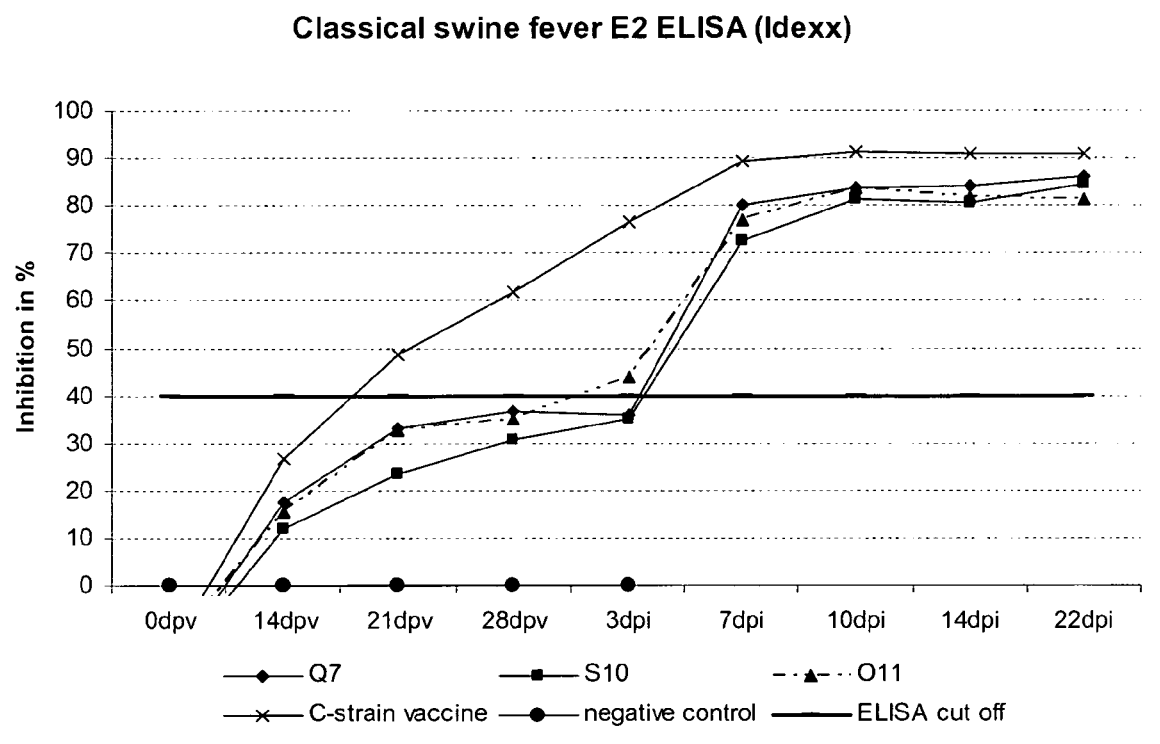

FIG. 4: The C-strain immunised animals showed positive results in the E2-ELISA 21 days after immunisation. 7 days after infection all immunised animals showed clearly positive results in the ELISA. The non-immunised control group showed no detectable antibodies after infection.

EXAMPLES

Experimental Design and Methods

Immunisation of Rabbits Using the TAV Peptide

Two 8-10 week old rabbits (ear tag 304 and 305) were immunised according to the following scheme, using a keyhole limpet hemocyanin (KLH)-conjugated CTAVSPTTL-RTEWK (SEQ ID NO. 6)-peptide in order to generate polyclonal C-strain neutralising serum. Immunisation was carried out followed by 6 boosts, each occurring at approximately month intervals.

Isolation of E2 Escape Variants of the C-Strain "Riems" Virus

In order to create antibody pressure with which to generate mutations of the C-strain "Riems" virus in glycoprotein E2, the virus was treated with various antibodies directed against the TAV-epitope of the E2 protein, using various concentrations. The infected cells were subsequently incubated and passaged a number of times. The antibodies which were applied in the present experiments are monoclonal E2 specific antibodies, which are commercially available for the E2 specific CSFV ELISA test.

Antibodies:
A181 (IDEXX)
A18B (Bommeli)
A18C (Ceditest)
HC34 (CRL, Hannover)
WH303 and WH 211 (Weybridge, Great Britain)

Incubation of the viral cultures was carried out according to the following. Various concentrations and mixtures of antibodies were applied with various amounts of virus. Incubation occurred for 2-6 hours at room temperature. The virus-antibody suspension was provided to cell culture plates with confluent cell growth and subsequently incubated. During this time, the virus was absorbed into the cells (PK15-cells) for 1-2 hours at 37° C. Finally the cell culture media was added and the plates were incubated for 72 hours at 37° C. and 5% COT.

After 72 hours the cell culture supernatants were individually separated and stored. The plates were then fixed and stained using immunofluorescence staining and a C16-antibody (specific for the NS3 protein from CSFV). The cell culture supernatant weak positive wells were then passaged under further antibody pressure as described above. Cell culture supernatants from wells with single positive cells or single stained cell plaques were then passaged under very weak or without antibody pressure in order to increase the virus titre for 1-2 passages. Various cell culture supernatants were selected for sequencing in E1 and E2 regions.

The controlling of escape variant virus was carried out using immunofluorescence staining with a C16 antibody or the A18 antibody used to produce the escape variants. Virus variants which exhibit a change in the TAV-epitope no longer can be stained using the A18 antibody.

Passage History

TABLE 3

Passage histories of the C-strain "Riems" escape viruses

| Variant O11 | | Variant Q7 | | Variant S10 | |
|---|---|---|---|---|---|
| Passage | Substitution | Passage | Substitution | Passage | Substitution |
| SP867/2 + A18(B)/HC34 (0.2 mg/ml) | | | | | |
| D5 + A18 (B, C) | 2870 | | | | |
| 16P1 + A18(B, I, C) je 0.25 mg/ml (50 µl) + 50 µl 305 | 2870 2122 | | | | |
| B1A1 + 0.25 mg/ml A18(C, B, I) (100 µl) + 100 µl 305 | | | | | |
| B5/2 | 2870, 2122, 2889, 3225 | | | | |
| B5/2-P2 (no pressure) | | | | | |
| B5/2-P3 (no pressure) | | | | | |
| B5/2-P3 + 0.1 mg A18(I) + 50 µl 304 | | | | | |
| B5/2-P3* + 0.1 mg A18 (I) + 50 ml 305 | | | | | |
| C32 + 50 µl A18 (I) + 50 µl 305 | | | | | |
| CB32-P2 (—) | 2870, 2122, 2889, 3225, 2862, 2099 | | | | |
| CB32-P3 + A18(I, C) every 50 µl, +305(25) | | | | | |
| Z2 + A18(I, C) 50 µl, +304/305 25 µl | | | | | |
| F8 + 304/305 30 µl | | | | | |
| G18 + 304 30 µl | | | | | |
| H15 (—) | | H15 (—) | 2870, 2122, 2889, 3225, 2862, 2099 | H15 + 304 50 µl | 2870, 2122, 2889, 3225, 2862, 2099 |
| I16 + A18(I, C) 50 µl + 10 µl HC34 + 304 25 µl | | I15 A18(I, C) 30 µl + 304 30 µl + HC34 15 µl | | I14 A18(I, C) 30 µl + 304 30 µl + HC34 15 µl | |
| K12 (—) | | O4 + A18 (I 50 µl, B 25 µl) + 304/305 25 µl | | N2 + A18(C 30 µl, I 50 µl) + 304 50 µl + 305 25 µl + HC34 15 µl | |
| L7 (—) | | P4 + 305 50 µl | | O6 + A18 (I 50 µl, B 25 µl) + 304/305 25 µl | |
| N17 (—) | | Q7 | | Q6 + A18 (I 50 µl, B 25 µl) + 304 50 µl | |
| O11 | 2870, 2122, 2889, 3225, 2862, 2099 | | | R9 + A18 I 50 µl + 304 50 µl | |
| | | | | S10 | |

Characterisation of the Escape Variants B5/2, I16, Q7, S10 and O11

The isolated escape variants were sequenced in the region of the E1 and E2 proteins. Various immunofluorescence stainings were carried out using the antibodies A18-idexx, A18-bommeli, A18-ceditest and the C16 antibody. The escape variants were passaged in both cell culture bottles (all) in addition to roller cultures (Q7, S10, O11) and were subsequently sequenced, differentially stained and titrated.

Q7 Specific Real-Time RT-PCR

In order to test the genetic characteristics of the virus, and thereby test one of the marker properties of the vaccine, detection of viral RNA after immunisation with the escape variants was carried out using primers and a probe, which were capable of distinguishing the escape variants from the original C-strain "Riems" and CSFV field isolates.

Animal Study 27/09—Testing the Immune Response of the C-Strain Riems Mutants B5/2-P6 and I16-P2

In the present animal studies, three piglets were each immunised with 2 ml of virus suspension (cell culture supernatant) via intramuscular application. The grouping of the animals was carried out as follows: group A (B5/2), group B (I16) and the control group C-strain Riems (Riemser swine fever vaccine). Serological test of the immune response were carried out for each group.

Animal Study 06/10—Testing the Escape Variants Q7, S10 and O11

The following animal studies were carried out in order to test which escape variants were the most promising in recipient pigs in regards to the absence of a dangerous effect and effectiveness after the intramuscular application.

21 piglets of 8-9 weeks of age (approx. 15-20 kg) were used in the study. Each piglet was immunised with $2 \times 10^{5.0}$ $KID_{50}$/ml, i.m.

5 groups were tested:
Group 1 (5 pigs): mutants of the C-strain variants Q7-P7 ($10^{5.0}$ $KID_{50}$/ml)
Group 2 (5 pigs): mutants of the C-strain variants S10-P8 ($10^{5.0}$ $KID_{50}$/ml)
Group 3 (5 pigs): mutants of the C-strain variants O11-P8 ($10^{5.0}$ $KID_{50}$/ml)
Group 4 (3 pigs): Riemser swine fever vaccine (raw virus)
Group 5 (3 pigs): unimmunised control group
Immunisation and blood sampling:
0 dpv Blood sampling (EDTA and Serum), immunisation
7 dpv Blood sampling (EDTA)
14 dpv Blood sampling (EDTA and Serum)
21 dpv Blood sampling (EDTA and Serum)
Data regarding body temperature and clinical symptoms were obtained daily.
Challenge:
28 dpv Blood sampling (EDTA and Serum), Nose swab
Challenge-Infection with the highly virulent KSPV Strain Koslov ($1 \times 10^{6.5}$ $KID_{50}$)
4 dpi Blood sampling (EDTA and Serum), Nose swab
7 dpi Blood sampling (EDTA and Serum), Nose swab
10 dpi Blood sampling (EDTA and Serum), Nose swab
14 dpi Blood sampling (EDTA and Serum), Nose swab
21 dpi Blood sampling (EDTA and Serum), Nose swab
28 dpi Blood sampling (EDTA and Serum), Nose swab
Animal Study 24/10—Testing the Escape Variants S10 and O11; Protection After Oral Immunisation In order to test the effectiveness of oral application, the following animal study was carried out. 15 piglets were used as test animals, which were 8-10 weeks old (approx. 15-20 kg).

Group 1 (6 pigs): mutants A C-strain variant S10
Group 2 (6 pigs): mutants B C-strain variant O11
Group 3 (3 pigs): infectious control (unvaccinated)

Immunisation and blood sampling:

| | |
|---|---|
| 0 dpv | Blood sampling (EDTA and Serum), Nose swab |
| 14 dpv | Blood sampling |
| 28 dpv | Blood sampling (EDTA and Serum), Nose swab |
| 4 dpi | Blood sampling (EDTA and Serum), Nose swab |
| 7 dpi | Blood sampling (EDTA and Serum), Nose swab |
| 10 dpi | Blood sampling (EDTA and Serum), Nose swab |
| 14 dpi | Blood sampling (EDTA and Serum), Nose swab |
| 21 dpi | Blood sampling |
| 28 dpi | Blood sampling |

Data regarding body temperature and clinical symptoms were obtained daily.

Experimental Results

Immunisation of Rabbits with the TAV-Peptide

Both rabbit serums (304 and 305) were positive in the commercially obtainable E2-ELISA test after the third boost treatment (approx. 12 weeks after the first immunisation). In the virus neutralisation test both serums tested positive approximately three weeks after the third boost. The titres in the neutralisation test were low and reduced further after the $4^{th}$-$6^{th}$ boost.

TABLE 4

Characterisation of the rabbit serum 304 and 305 after TAV-peptide immunisation

| Serum | E2 ELISA IDEXX Inhibition in % | NT Alfort | Note |
|---|---|---|---|
| 304 | 6 | <5 | 1. immunisation |
| 305 | 10 | <5 | |
| 304 | 28 | <5 | 1. Boost |
| 305 | 19 | <5 | |
| 304 | 45 | <5 | 2. Boost |
| 305 | 26 | <5 | |
| 304 | 87 | 5 | 3. Boost |
| 305 | 60 | <5 | |
| 304 | 90 | 10 | 4. Boost |
| 305 | 77 | 5 | |
| 304 | Not carried out | 5 | 2 weeks after 5. Boost |
| 305 | Not carried out | <5 | |
| 304 | Not carried out | 7.5 | 1 weeks after 6. Boost |
| 305 | Not carried out | <5 | |
| 304 | Not carried out | <5 | 3 weeks after 6. Boost |
| 305 | Not carried out | <5 | |

Isolation of E2 Escape Variants of the C-Strain Riems Virus

Incubation of the C-strain Riems with E2 specific antibodies led, after only a few passages, to the isolation of escape variants that exhibited one substitution in the E2 region at position 2870. It was important for the isolation of further variants that a compensatory change in the E1 protein at position 2122 also occurred, for example as in isolate 16P1. If both changes occurred simultaneously, then only a few passages were required under the antibody and serum pressure in order to isolate further variants which additionally exhibited a substitution at position 2889 in the E2 protein. Some of these escape variants demonstrated additionally a change at position 3225 in the E2 protein. An example of such an escape variant is the isolate B5/2.

Schematic representation of the TAV-epitope of the variant B5/2:

```
Wildtyp C-Stamm:
CTAVSPTTLRTEVVK

Mutante B5/2:
CTAVSSTTLRTGVVK
```

Further passaging of the B5/2 isolate under antibody pressure led to isolation of the CB32 isolate. This isolate exhibited additionally a further substitution in the E2 protein (nucleotide 2862), in addition to a compensatory substitution in the E1 protein at position 2899. The isolate CB32 resulted from a mixture of the variants B5/2 and a new variant with the additional substitution. In order to isolate the new variants which exhibited the additional substitutions, the isolate CB32 was passaged for multiple passages under antibody pressure. From a subsequent and joined passage H15 the isolates Q7, S10 and O11 were isolated.

See FIG. 1 for a sequence comparison of the TAV-epitope of the S10, O11 and Q7 mutant. See Table 1 for a review of the nucleotide and amino acid substitutions in the isolated escape variants.

Characterisation of the Escape Variants B5/2, I16, Q7, S10 and O11

Testing of the escape variants regarding the binding of various E2 specific antibodies was carried out using immunofluorescence.

TABLE 7

Immunofluorescence staining of particular passages of various E2 escape variants, exhibiting three substitutions in the TAV-epitope

| E2 Mutants | A18 Idexx 1:400 | A18 Bommeli 1:250 | A18 Ceditest 1:500 | 303 1:100 | 211 1:100 | C16 1:90 |
|---|---|---|---|---|---|---|
| I16-P3 | − | − | − | − | − | +++ |
| Q7-P8 | − | − | − | − | − | +++ |
| O11-P7 | − | − | − | − | − | +++ |
| S10-P8 | − | − | − | 1 colony | − | +++ |
| C-strain | +++ | +++ | +++ | +++ | +++ | +++ |

All tested isolates demonstrated negative signals for the selected passages for A18 stainings. However at the 8$^{th}$ passage of the S10 isolate, a small colony was stainable using the antibody WH303. This supports a high stability of substitutions in the TAV-epitope. Further stability tests were carried out for the Q7, S10 and O11 isolates, using roller cultures over 10 additional passages.

TABLE 8

Differential staining of selected passages with the antibodies A18 (idexx and bommeli and WH303 (VLA). The NS3 specific antibody C16 (EURL) was used for control purposes

| Sample | Q7-P10 | Q7-P14 | Q7-P16 | S10-P10 | S10-P14 | S10-P16 | O11-P10 | c-strain | antibody |
|---|---|---|---|---|---|---|---|---|---|
| Idexx | − | − | − | − | (+; EZ) | (+; EZ) | − | +++ | Idexx |
| Bommeli | − | − | − | − | − | − | − | +++ | Bommeli |
| WH303 | − | − | − | − | − | − | − | +++ | WH 303 |
| C16 | +++ | +++ | − | +++ | +++ | +++ | +++ | +++ | C16 |
| O11-P14 | − | − | − | +++ | − | − | − | − | |
| O11-P16 | − | (+; EZ) | (+; EZ) | +++ | − | − | − | − | |
| Antikörper | Idexx | Bommeli | WH303 | C16 | | | | | |

EZ = a few single cells

TABLE 5

Indirect immunofluorescence staining of selected E2 escape variants with a substitution in the E2 protein

| E2 Mutants | C16 CSF-NS3B | A18Bommeli CSF-E2 |
|---|---|---|
| SNT | positive | negative |
| 16P1 | positive | negative |
| 25P3 | positive | negative |
| 60P3 | positive | negative |
| 12P5 | positive | negative |
| 34P5 | positive | positive |
| 50P5 | positive | negative |
| 51P5 | positive | negative |
| 5P6 | positive | negative |
| 48P6 | positive | negative |
| 59P7 | positive | negative |
| 60P7 | positive | negative |
| C-Stamm | positive | positive |
| Alfort | positive | positive |

In most cases, a single amino acid substitution in the TAV-epitope was sufficient to provide a negative signal when using immunofluorescence with the A18Bommeli antibody. Escape variants with two TAV mutations (such as B5/2) also showed negative results with both A18Bommeli and the A18C antibodies (FIG. 2).

At the 10$^{th}$ passage, there was no virus variant that demonstrated a reversion, so that the staining was only possible with C16. The variant Q7 was negative for all stainings until the 14$^{th}$ passage, whereby in the 16$^{th}$ passage was also unable to be detected with the C16 antibody. These findings were confirmed using RT-PCR in addition to sequencing PCR protocols. It is therefore clear that no virus is present at the 16$^{th}$ passage, so that a passaging error can also be excluded. Some cells could however be stained in the 14$^{th}$ and 16$^{th}$ passages of the S10 isolate using the A18 (idexx) antibody. For the mutant O11, 16 passages were carried out before some single cells could be stained using the A18 (bommeli) and WH303 antibodies. These results demonstrate the high stability of the serological characteristics of the viral vaccines as described herein.

Characterisation of the Escape Variants via Sequencing of E1 and E2

TABLE 9

Sequencing of earlier isolates exhibiting a substitute in the TAV-epitope of the E2 protein

| Mutants | sequencing original | sequencing 10th passage |
|---|---|---|
| 48P6 | Substitution 2870 | Substitution 2870 |
| 2SNTP1 | Substitution 2870 | Substitution 2870 |

TABLE 9-continued

Sequencing of earlier isolates exhibiting a substitute in the TAV-epitope of the E2 protein

| Mutants | sequencing original | sequencing 10th passage |
|---|---|---|
| 59P7 | Substitution 2870 | Substitution 2870 |
| 60P7 | Substitution 2870 | Substitution 2870 |
| 5P6b | Substitution 2870 | Substitution 2870 |
| D9 | Substitution 2870 | Substitution 2870 |
| E51 | Substitution 2870 | Substitution 2870 |
| E52 | Substitution 2870 | Substitution 2870 |
| 16P1 | Substitution 2870, Substitution 2122 | Substitution 2870, Substitution 2122 |

The substitution at position 2870 was maintained in all isolates after 10 passages, which seems to be very stable. This supports the conclusion that this particular substitution has no large effect on the structure of the protein, so that a reversion to the wild type sequence provides no advantage.

TABLE 10

Sequencing of isolates with 3 substitutions in the E2 TAV-epitope

| E2 Mutant | Virus Titer/ml | substitution $E^{RNS}$ | substitution E1 | substitution E2 | Stabile Mutations |
|---|---|---|---|---|---|
| I16-P3 | $10^{5.25}$ | 1649 | 2099 2122 | 2862 (80%) 2870 2889 3225 | I16-P24 1649, (1657, 1878) 2122, 2870, 2889 |
| Q7-P8 | $10^5$ | 1649 | 2099 2122 | 2862 2870 2889 3225 | Q7-P17 1649, 2099, 2122 2862, 2870, 2889, 3225 |
| O11-P7 | $10^5$ | 1649 | 2099 2122 | 2862 2870 2889 3225 | O11-P14 1649, 2099, 2122 2862, 2870, 2889, 3225 |
| S10-P8 | $10^5$ | 1649 | 2099 2122 | 2862 2870 2889 3225 | S10-P15 1649, 2099, 2122 2862, 2870, 2889, 3225 |

The changes in sequence in the isolates O11, S10 and Q7 were stable for all tested passages (14-17).

TABLE 11

Sequencing of the isolates Q7, S10 and O11 after various passages in roller cultures

| Sample | Q7-P10 | Q7-P14 | Q7-P16 | S10-P10 | S10-P14 | S10-P17 | O11-P9 | O11-P14 | O11-P16 |
|---|---|---|---|---|---|---|---|---|---|
| E1-Protein | 2099 2122 | 2099 2122 | not sequenced | 2099 2122 | 2099 2122 | 2099 2122 | n.d. n.d. | 2099 2122 | 2099 2122 |
| E2-Protein | 2862 2870 2889 | | | 2862 2870 2889 | 2862 2870 2889 | 2862 2870 2889 | 2862 2870 2889 | 2862 2870 2889 | 2862 2870 2889 |

All sequenced virus passages of the three variants contained the substitutions in the E1 and E2 proteins that had been induced by immune pressure. The 16th passage of Q7 could not be sequenced, likely because no virus was remaining in the cell culture supernatant (see above). In the case that revertant viruses do appear, which based on the various stainings in FIG. 2 cannot be excluded, they are only detectable by sequencing as of a determined percentage. The enormous majority of the viruses is however not reverted and remains substituted. Single individual reverted viruses could not be detected by sequencing.

Q7 Specific Real-Time RT-PCR

In order to differentiate between vaccinated and infected animals, an RT-PCR system was applied. Because the TAV-epitope is highly conserved in all CSF viruses, the substitutions in the TAV-epitope were used as a basis for primers and probes in the real-time PCR assay.

TABLE 13

Real-time RT-PCR was used to control the virus burden. The following PCR systems were applied: CSF Mix 1 (CSFV specific, recognises all strains), Q7-TAV (specific for the variants) and C-strain-TAV mix (C-strain wild type, with a much lower sensitivity can also be detected). The results are provided as Ct values (cycle threshold).

| System | Q7-P10 | Q7-P14 | Q7-P16 | S10-P10 | S10-P14 | S10-P17 | O11-P9 | O11-P14 | O11-P16 |
|---|---|---|---|---|---|---|---|---|---|
| CSF Mix1 | 21.2 | 20.4 | n.d. | 20.5 | 19.2 | 20.1 | 20.1 | 19.5 | 20.1 |
| C-strain TAV-Mix | 36.5 | 35.7 | 37.8 | 34.9 | 31.2 | 30.2 | 35.8 | 33.6 | 33 |

TABLE 13-continued

Real-time RT-PCR was used to control the virus burden. The following PCR systems were applied: CSF Mix 1 (CSFV specific, recognises all strains), Q7-TAV (specific for the variants) and C-strain-TAV mix (C-strain wild type, with a much lower sensitivity can also be detected). The results are provided as Ct values (cycle threshold).

| System | Sample | | | | | | | | |
|---|---|---|---|---|---|---|---|---|---|
| | Q7-P10 | Q7-P14 | Q7-P16 | S10-P10 | S10-P14 | S10-P17 | O11-P9 | O11-P14 | O11-P16 |
| Q7-TAV rRT-PCR | 22.4 | 21.9 | 27.3 | 21.4 | 20.9 | 21 | 20.9 | 20.2 | 21.6 |

The virus load was determined using real-time RT-PCR. The CSF-Mix 1 system recognised all CSFV strains and did not differentiate between the C-strain wild type and the new escape variants. The Q7-TAV system recognised all three escape variants specifically. The C-strain-TAV system only recognised the C-strain wild type (none of the escape variants), with a ct value of approximately 14.

The very small reduction in the difference in the Ct values between the Q7-TAV RT-PCR system and the C-strain-TAV system with increasing number of passages provides strong evidence for a very small amount of revertants after high numbers of passages. In general, a difference between the two systems of 14 Ct values represent a ratio of mutants to revertants of approx. 1:8000, whereby a Ct value of 10 represents a ratio of 1:1000.

Animal Study 27/09—Examination of the Immune Response of the C-Strain Riems Mutants B5/2-P6 and I16-P2

Intramuscular immunisation was carried out with 3 piglets, whereby each piglet received 2 ml of virus suspension (cell culture supernatant). Group A was treated with B5/2, group B was treated with I16 and the control group was treated with the Riemser swine fever vaccine. These studies provide analysis of the immune response after immunisation, test the marker properties of the vaccination after modified immune response (ELISA) and test the properties of the virus in vaccinated animals (genetic stability and replication properties).

A back titration of the applied viruses provided the following results:

B5/2-P6: Virus titre $10^{4.25}$ virus/ml
I16-P2: Virus titre $10^{4.75}$ virus/ml Tolerance of the Animals to the Vaccine The treated pigs demonstrated no obvious symptoms after immunisation (no fever or symptoms of illness). The number of leucocytes was not increased above normal for the first 7 days after immunisation.

The virus could not be isolated from blood. RNA isolated from the blood samples 4 days and 7 after immunisation was used for RT-PCR analysis. The PCR product was however unsuitable for a subsequent sequencing. This demonstrates a very low replication rate of the virus in the animals.

Animal Study 06/10—Testing the Escape Variants Q7, S10 and O11

Back-titration revealed the following concentrations of virus, which were used in the experiments:

| Q7-P8 | $10^{4.0}$ KID$_{50}$/ml |
| S10-P8 | $10^{4.25}$ KID$_{50}$/ml |
| O11-P7 | $10^{4.25}$ KID$_{50}$/ml |
| C-strain swine fever vaccine | $10^{2.25}$ KID$_{50}$/ml |

After immunisation, there were neither changes in body temperature nor illness symptoms typical for swine fever to be found.

Clinical Analysis After Challenge Infection

Fever was defined as a rectal body temperature of >40° C. for at least two successive days.

5 groups were tested:
Group 1 (5 pigs): mutants of the C-strain variants Q7-P7 ($10^{5.0}$ KID$_{50}$/ml)
Group 2 (5 pigs): mutants of the C-strain variants S10-P8 ($10^{5.0}$ KID$_{50}$/ml)
Group 3 (5 pigs): mutants of the C-strain variants O11-P8 ($10^{5.0}$ KID$_{50}$/ml)
Group 4 (3 pigs): Riemser swine fever vaccine (raw virus)
Group 5 (3 pigs): unimmunised control group In group 1 sporadic increased temperature measurements between the 3$^{rd}$ and 13$^{th}$ day after challenge infection, which were however not related to any other visible disruption in the well-being of the animal subjects. Only animal no. 4 demonstrated fever over 4 days.

Group 2 exhibited sporadic increases in temperature in 3 treated animals, whereby animal no. 9 demonstrated significant high temperatures.

In group 3 only animal no. 14 demonstrated an increased body temperature with fever on the 4$^{th}$ and 5$^{th}$ day after challenge infection.

The animals of group 4 did not demonstrate fever, whereby sporadic temperature increase was measured in 2 treated animals.

All animals of group 5 demonstrated fever between the 2$^{nd}$ and 7$^{th}$ day after infection. Due to significant swine fever symptoms all animals of group 5 were sacrificed 7 days after infection. The most common symptoms were effects to the central nervous system (hind leg pareses and ataxia, diarrhoea, conjunctivitis and somnolence). One animal demonstrated haematoma of the skin.

The virus was unable to be isolated from immunised animals from nose swabs, whereby the unvaccinated control animals tested positive 7 days after infection.

RT-PCR Results with Serum Samples

RT-PCR results demonstrated that after 14 days post infection only very weak signals could be obtained from immunised animals when testing for the presence of the virulent disease-associated virus. However, the non-vaccinated control animals demonstrated strong positive signals with positive Ct values of 30 or less 3 days after infection. The Ct values from non-vaccinated animals dropped to 17 after 7 days.

RT-PCR Results from Nose Swabs

The RT-PCR results from immunised animals were solely negative. The non-vaccinated control animals however demonstrated a strong positive signal with Ct values between 25 and 28 7 days after infection.

Virus Neutralisation Test with CSFV Alfort

The virus neutralisation test relates to the determination of whether animals (either vaccinated or non-vaccinated) exhibit antibodies that are capable of neutralising virulent virus. All immunised groups showed neutralising antibodies 21 days after immunisation. 7 days after infection the virus neutralisation test titre against Alfort was 640 $ND_{50}$ or more, in all immunised groups. One animal in the O11 immunised group and one animal in the C-strain control group exhibited a titre of 480. The non-immunised control animals exhibited no virus titre against Alfort in the VNT.

Virus Neutralisation Test (VNT) with CSFV Rösrath

See FIG. 3 for VNT with the CSFV strain Rösrath.

Three weeks after immunisation all animals, with the exception of one animal in the S10 group and one animal in the O11 group, showed neutralising antibodies. 7 days after infection the immunised animals demonstrated in general a VNT titre of 640 or larger. The lowest titre was 320, shown by one animal in the TAV mutant immunised group. The non-immunised control animals exhibited no titre in the VNT against Rösrath.

E2-ELISA (idexx)

The E2-ELISA is a commercially available ELISA-kit for testing for the presence of classical swine fever. On average, the C-strain immunised animals showed positive results in the E2-ELISA 21 days after immunisation. The animals immunised with TAV mutants also showed positive results after 7 days in the idexx E2-ELISA. The non-immunised control group showed no detectable antibodies after infection.

See FIG. 4 for the Idexx E2-ELISA with pig serum.

In the E2-ELISA, results for the TAV mutants before infection were positive, but not strong, whereas after infection the results became strongly positive, which suggests a strong booster effect. The C-strain immunised control animals were strongly positive in the E2-ELISA before infection.

The results of the animals immunised with the TAV mutants are comparable with the animals immunised with the C-strain control group. Isolation of virus after infection was negative and the RT-PCR results were questionable or weakly positive, which was also demonstrated in the C-strain control group. All animals exhibited high titres in the virus neutralisation test against Alfort in addition to Rösrath. All immunised animals demonstrated complete protection against the infective virus strain Koslov four weeks after intramuscular immunisation.

Animal Study 24/10—Testing of the Escape Variants S10 and O11; Protection After Oral Immunisation In order to test the effectiveness of oral application, the following animal study was carried out. 15 piglets were used as test animals, which were 8-10 weeks old (approx. 15-20 kg).

Vaccination dose and experimental design:

Group 1 (6 pigs): mutants A C-strain variant S10 ($10^5$ $KID_{50}$/ml)

Group 2 (6 pigs): mutants B C-strain variant O11 ($10^4$ $KID_{50}$/ml)

Group 3 (3 pigs): infectious control (unvaccinated)

Group 1: All animals of this group were completely protected before the challenge infection. No illness-associated symptoms were detected. All animals showed neutralising antibodies, which were detectable by both the VNT and the ELISA tests.

Group 2: Animals in Group 2 demonstrated a mixture of protection and infection. 2 animals demonstrated illness symptoms, such as high fever and other typical swine fever symptoms. The affected animals were euthanized. The protected animals showed neutralising antibodies, which were detectable by both the VNT and the ELISA tests.

Group 3: All animals were infected and showed illness symptoms. The affected animals were euthanized.

The oral immunisation study demonstrates that oral immunisation, especially using the S10 mutant, leads to effective protection from infection. The O11 isolate also demonstrated beneficial results, considering the vaccination dose was reduced in comparison to the S10 administered virus.

LITERATURE

Council Directive 2001/89/EC of 23 Oct. 2001 on Community measures for the control of classical swine fever (2001): Official Journal of the European Communities L 316, 5-35.

Diagnostic Techniques and Vaccines for Foot-and-Mouth Disease, Classical Swine Fever, Avian Influenza and some other important OIE List A Diseases (2003a): Report of the Scientific Committee on Animal Health and Animal Welfare Adopted 24-25 Apr. 2003, 1-150.

Report on the evaluation of a new classical swine fever discriminatory test (2003/265/EC) (2003b).

Commission Decision of 23 Nov. 2006 approving the plans for the eradication of classical swine fever in feral pigs and the emergency vaccination of those pigs and of pigs in holdings against that disease in Romania (2006/802/EC) (2006): Official Journal of the European Union L329, 34-37.

Beer, M, Reimann, I, Hoffmann, B, Depner, K (2007): Novel marker vaccines against classical swine fever. Vaccine 25 (30): 5665-5670.

Blome, S, Meindl-Bohmer, A, Loeffen, W, Thuer, B, Moennig, V (2006): Assessment of classical swine fever diagnostics and vaccine performance. Rev Sci Tech 25 (3): 1025-1038.

de Smit, A J, Bouma, A, Van Gennip, H G, de Kluijver, E P, Moormann, R J (2001): Chimeric (marker) C-strain viruses induce clinical protection against virulent classical swine fever virus (CSFV) and reduce transmission of CSFV between vaccinated pigs. Vaccine 19 (11-12): 1467-1476.

Dong, X N, Chen, Y H (2007): Marker vaccine strategies and candidate CSFV marker vaccines. Vaccine 25 (2): 205-230.

Floegel-Niesmann, G (2003): Marker vaccines and companion diagnostic tests for classical swine fever. Dev Biol (Basel) 114, 185-191.

Greiser-Wilke, I, Moennig, V (2004): Vaccination against classical swine fever virus: limitations and new strategies. Anim Health Res Rev 5 (2): 223-226.

Leifer, I, Lange, E, Reimann, I, Blome, S, Juanola, S, Duran, J P, Beer, M (2009): Modified live marker vaccine candidate CP7_E2alf provides early onset of protection against lethal challenge infection with classical swine fever virus after both intramuscular and oral immunization. Vaccine.

Van Oirschot, J T (2003): Vaccinology of classical swine fever: from lab to field. Vet Microbiol 96 (4): 367-384.

Vandeputte, J, Chappuis, G (1999): Classical swine fever: the European experience and a guide for infected areas. Rev Sci Tech 18 (3): 638-647.

Diagnostic Techniques and Vaccines for Foot-and-Mouth Disease, Classical Swine Fever, Avian Influenza and some other important OIE List A Diseases: European Commission, Directorate-General for Health and Consumer Protection, Brussels; 2003 p. 1-150.

Koenig P, Lange E, Reimann I, Beer M. CP7_E2alf: a safe and efficient marker vaccine strain for oral immunisation of wild boar against Classical swine fever virus (CSFV). Vaccine 2007 Apr. 30; 25(17):3391-9.

Floegel-Niesmann G. Classical swine fever (CSF) marker vaccine. Trial III. Evaluation of discriminatory ELISAs. Vet Microbiol 2001 Nov. 8; 83(2):121-36.

D. Luetticken, C. Drexler, N. Visser and V. Kaden, The relevance of CSF marker vaccines for field use, Proceedings of OIE symposium on classical swine fever (Hog Cholera) Birmingham, U.K., July 9-10 (1998).

J. T. van Oirschot, Diva vaccines that reduce virus transmission, J Biotechnol 73 (2-3) (1999), pp. 195-205.

A. Uttenthal, M. F. Le Potier, L. Romero, G. M. DeMia and G. Floegel-Niesmann, Classical swine fever (CSF) marker vaccine Trial I. Challenge study in weaner pigs, Vet Microbiol 83 (2) (2001), pp. 85-106.

K. R. Depner, A. Bouma, F. Koenen, D. Klinkenberg, E. Lange and H. de Smit et al., Classical swine fever (CSF) marker vaccine Trial II: Challenge study in pregnant sows, Vet Microbiol 83 (2) (2001), pp. 107-120.

A. J. de Smit, H. G. van Gennip, G. K. Miedema, P. A. van Rijn, C. Terpstra and R. J. Moormann, Recombinant classical swine fever (CSF) viruses derived from the Chinese vaccine strain (C-strain) of CSF virus retain their avirulent and immunogenic characteristics, Vaccine 18 (22) (2000), pp. 2351-2358.

Yan Li et al, A multiplex nested RT-PCR for the detection and differentiation of wild-type viruses from C-strain vaccine of classical swine fever virus.

Y. Qi, et al, Characterization of antibody responses against a neutralizing epitope on the glycoprotein E2 of classical swine fever virus.

Jian-Jun Zhao et al, Evaluation of a multiplex real-time RT-PCR for quantitative and differential detection of wild-type viruses and C-strain vaccine of Classical swine fever virus.

Susana Mendozaa et al, Antigenic differentiation of classical swine fever vaccinal strain PAV250 from other strains, including field strains from Mexico.

J. Kortekaas et al, Rational design of a classical swine fever C-strain vaccine virus that enables the differentiation between infected and vaccinated animals, 2009.

L. G. Holinka et al: Development of live attenuated antigenic marker classical swine fever vaccine, Virology, 2009.

Hulst et al, Passage of Classical Swine Fever Virus in Cultured Swine Kidney Cells Selects Virus Variants That Bind to Heparan Sulfate due to a Single Amino Acid Change in Envelope Protein Ems, Journal of Virology, October 2000, p. 9553-9561 Vol. 74, No. 20.

The invention claimed is:

1. A marker vaccine for prophylactic treatment of classical swine fever comprising: a modified live attenuated classical swine fever virus having an E2 protein comprising a viral amino acid sequence of a TAV-epitope, wherein said viral amino acid sequence of the TAV-epitope of the E2 protein comprises a sequence that differs from that of a wild-type classical swine fever virus, wherein the viral amino acid sequence comprises at least one of the following substitutions with reference to a numbering of the viral amino acid sequence of a C-strain "Riems" virus:
   substitution of amino acid 830 to valine,
   substitution of amino acid 839 to glycine.

2. The marker vaccine according to claim 1, wherein the modified virus is not produced via recombinant DNA methods.

3. The marker vaccine according to claim 1, wherein the viral amino acid sequence comprises one or more of the following substitutions with reference to C-strain "Riems" virus:
   substitution of amino acid 426; in protein $E^{RNS}$ to valine,
   substitution of amino acid 576; in protein E1 to histidine,
   substitution of amino acid 583; in protein E1 to glutamic acid,
   substitution of amino acid 951; in protein E2 to isoleucine.

4. The marker vaccine according to claim 1, wherein the viral nucleotide sequence comprises one or more of the following substitutions with reference to the numbering of the viral amino acid sequence of the C-strain "Riems" virus:
   substitution at nucleotide position 1649 to G,
   substitution at nucleotide position 2099 to C,
   substitution at nucleotide position 2122 to G,
   substitution at nucleotide position 3225 to T.

5. The marker vaccine according to claim 1, wherein the viral amino acid sequence of the TAV-epitope comprises a sequence according to SEQ ID NO. 3 or SEQ ID NO. 4.

6. A pharmaceutical composition comprising the marker vaccine of claim 1 with a pharmaceutically acceptable carrier.

7. A method for the prophylactic treatment of classical swine fever comprising:
   administering the marker vaccine according claim 1 to a subject in an amount effective for the prophylactic treatment of classical swine fever.

8. The method of claim 7, wherein the subject is a pig.

9. The method of claim 7, wherein the administering is via intramuscular injection.

10. The method of claim 7, wherein the administering is via oral application.

11. The marker vaccine according to claim 1, wherein the viral amino acid sequence comprises the substitution of amino acid 839 to glycine.

12. The marker vaccine according to claim 1, wherein the viral amino acid sequence comprises the substitution of amino acid 830 to valine, and the substitution of amino acid 839 to glycine.

13. The marker vaccine according to claim 1, wherein the viral amino acid sequence comprises the substitution of amino acid 426 in protein $E^{RNS}$ to valine, the substitution of amino acid 576 in protein E1 to histidine, the substitution of amino acid 583 in protein E1 to glutamic acid and the substitution of amino acid 951 in protein E2 to isoleucine.

14. The marker vaccine according to claim 12, wherein the viral amino acid sequence exhibits comprises the substitution of amino acid 426 in protein $E^{RNS}$ to valine, the substitution of amino acid 576 in protein E1 to histidine, the substitution of amino acid 583 in protein E1 to glutamic acid and the substitution of amino acid 951 in protein E2 to isoleucine.

* * * * *